US00PP36540P2

(12) United States Plant Patent
Koene

(10) Patent No.: US PP36,540 P2
(45) Date of Patent: Mar. 11, 2025

(54) ***MANDEVILLA* PLANT NAMED 'Sunpa 13872'**

(50) Latin Name: *Mandevilla hybrida*
Varietal Denomination: Sunpa 13872

(71) Applicant: Tim Koene, Maasland (NL)

(72) Inventor: Tim Koene, Maasland (NL)

(73) Assignee: SUNTORY FLOWERS LIMITED, Tokyo (JP)

( * ) Notice: Subject to any disclaimer, the term of this patent is extended or adjusted under 35 U.S.C. 154(b) by 18 days.

(21) Appl. No.: 18/624,029

(22) Filed: Apr. 1, 2024

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Mandevilla* plant named 'Sunpa 13872', characterized by its vining and climbing plant habit; vigorous growth habit; freely branching habit; freely flowering habit; long flowering period; flowers that are purplish red and light purplish pink bi-colored; and good garden performance.

2 Drawing Sheets

Figure 1:
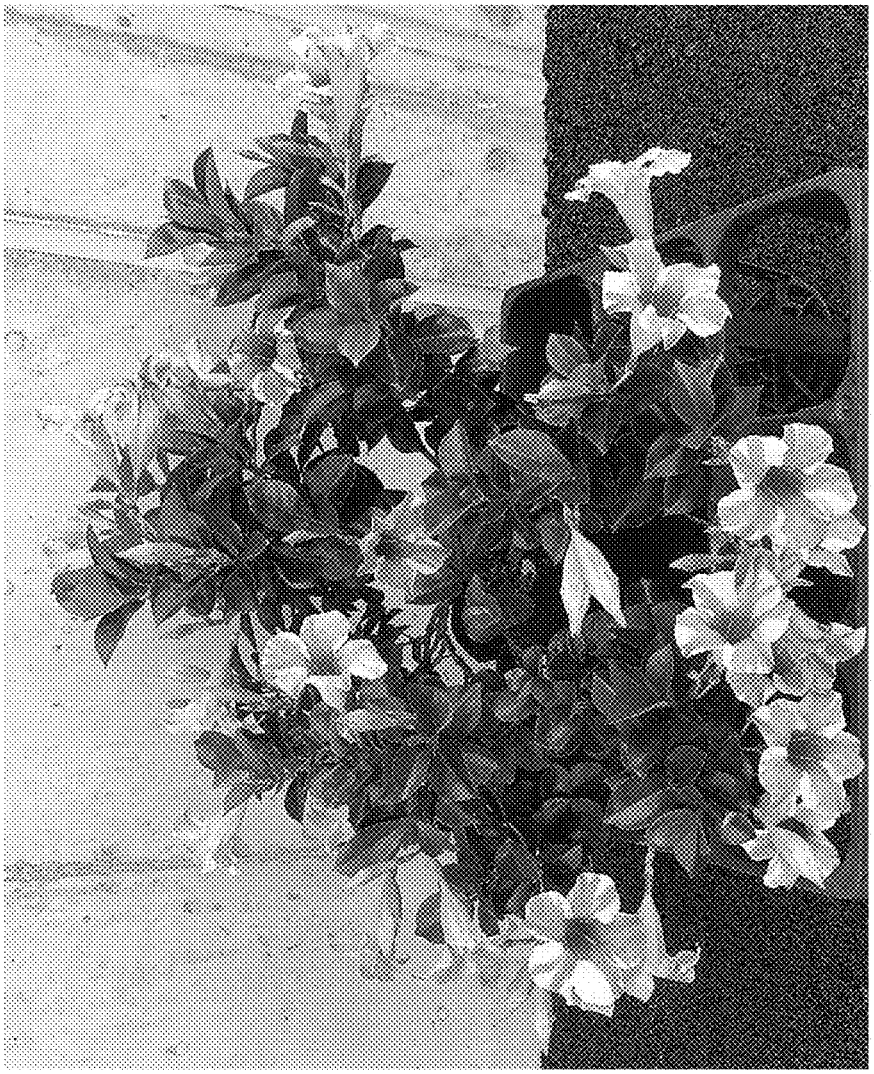

Botanical designation: *Mandevilla hybrida.*
Cultivar denomination: 'SUNPA 13872'.

STATEMENT REGARDING PRIOR DISCLOSURES BY INVENTOR/APPLICANT and ASSIGNEE

The Inventor/Applicant and Assignee assert that no sales, offers for sale or public distribution of the instant plant occurred more than one year prior to the effective filing date of this application.

Any information about the claimed plant would have been obtained from a direct or indirect disclosure from the Inventor/Applicant and/or Assignee. Inventor/Applicant and Assignee claim a prior art exception under 35 U.S.C. 102 (b)(1) for disclosures and/or sales prior to the filing date but less than one year prior to the effective filing date.

BACKGROUND OF THE INVENTION

The present invention relates to a new and distinct cultivar of *Mandevilla* plant, botanically known as *Mandevilla hybrida* and hereinafter referred to by the name 'Sunpa 13872'.

The new *Mandevilla* plant is a naturally-occurring branch mutation of *Mandevilla hybrida* 'Sunpa 201', disclosed in U.S. Plant Pat. No. 34,565. The new *Mandevilla* plant was discovered and selected by the Inventor on a single flowering plant from within a population of plants of 'Sunpa 210' in a controlled greenhouse environment in Maasland, The Netherlands in June 2022.

Asexual reproduction of the new *Mandevilla* plant by terminal vegetative cuttings in Maasland, The Netherlands since June 2022 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 13872'. These characteristics in combination distinguish 'Sunpa 13872' as a new and distinct *Mandevilla* plant:

1. Vining and climbing plant habit.
2. Vigorous growth habit.
3. Freely branching habit.
4. Freely flowering habit.
5. Long flowering period.
6. Flowers that are purplish red and light purplish pink bi-colored.
7. Good garden performance.

Plants of the new *Mandevilla* can be compared to plants of the mutation parent, 'Sunpa 201'. Plants of the new *Mandevilla* differ primarily from plants of 'Sunpa 201' in flower color as plants of the new *Mandevilla* have purplish red and light purplish pink bi-colored flowers whereas plants of 'Sunpa 201' have speckled red and light purplish pink bi-colored flowers.

Plants of the new *Mandevilla* can be compared to plants of the *Mandevilla hybrida* 'Sunpa 4411', disclosed in U.S. Plant Pat. No. 33,141. In side-by-side comparisons, plants of the new *Mandevilla* differ from plants of 'Sunpa 4411' in the following characteristics:

1. Plants of the new *Mandevilla* have smaller leaves than plants of 'Sunpa 4411'.
2. Plants of the new *Mandevilla* have larger flowers than plants of 'Sunpa 4411'.
3. Flowers of plants of the new *Mandevilla* face more outwardly than and not as upright as flowers of plants of 'Sunpa 4411'.
4. Flower petals of plants of the new *Mandevilla* are imbricate whereas flower petals of plants of 'Sunpa 4411' are not imbricate.

5. Plants of the new *Mandevilla* have purplish red and light purplish pink bi-colored flowers with purplish red-colored throats whereas plants of 'Sunpa 411' have purplish red-colored flowers with yellow-colored throats.
6. Plants of the new *Mandevilla* have shorter peduncles than plants of 'Sunpa 4411'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1) is a side perspective view of a typical flowering plant of 'Sunpa 13872' grown in a container.

Figure 2:
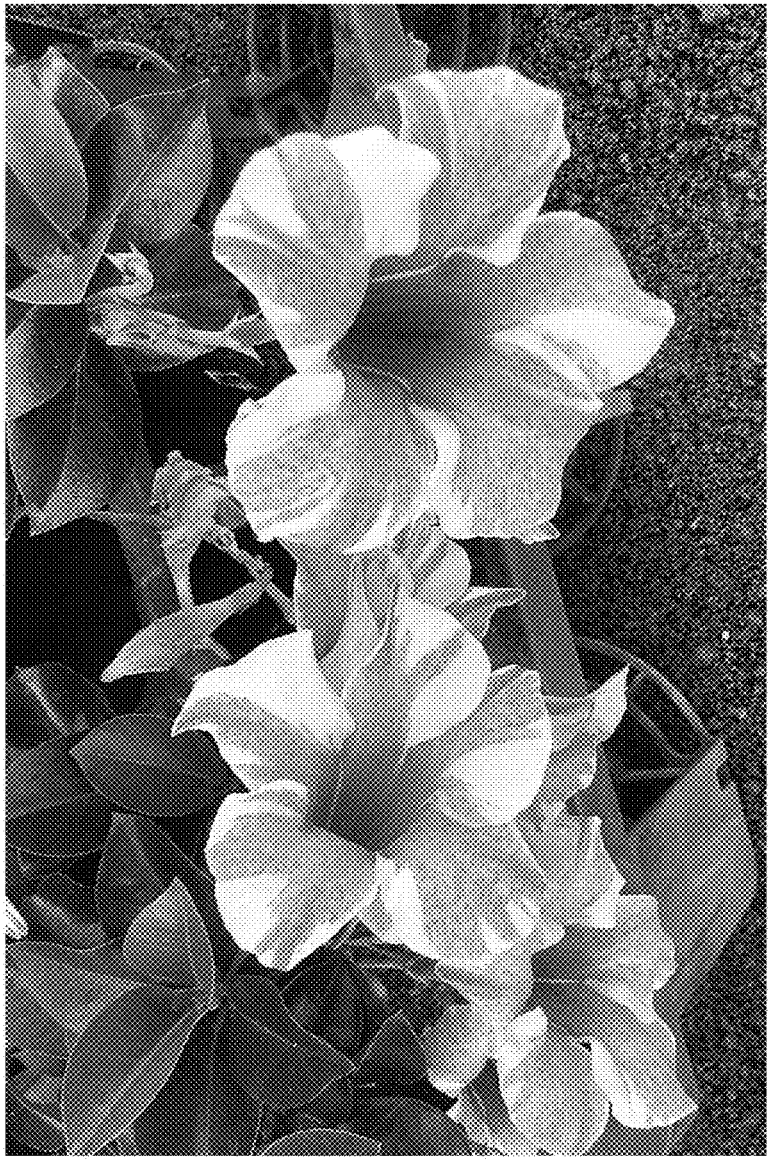

The photograph on the second sheet (FIG. 2) is a close-up view of a typical flowering plant of 'Sunpa 13872'.

DETAILED BOTANICAL DESCRIPTION

The aforementioned photographs and following observations, measurements and values describe plants grown during the early summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2015 Edition, except where general terms of ordinary dictionary significance are used.

Botanical classification: *Mandevilla hybrida* 'Sunpa 13872'.

Parentage: Naturally-occurring branch mutation of *Mandevilla hybrida* 'Sunpa 201', disclosed in U.S. Plant Pat. No. 34,565.

Propagation:

*Type*.—By terminal vegetative cuttings.

*Time to initiate roots, summer and winter*.—About two weeks at temperatures about 23° C. to 25° C.

*Time to produce a rooted young plant, summer and winter*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Vining and climbing plant habit; vigorous growth habit; freely branching habit; suitable for hanging baskets and garden plantings.

*Lateral branch description*.—Length: About 16.8 cm. Diameter: About 2.6 mm. Internode length: About 2.7 cm. Strength: Strong, flexible. Texture: Smooth, glabrous. Color, developing: Close to 138B variably tinged with close to 152A. Color, fully developed: Close to 177C.

Leaf description:

*Arrangement and quantity*.—Decussate, simple; medium density, about 17 per lateral branch.

*Length*.—About 5.2 cm.

*Width*.—About 4 cm.

*Shape*.—Ovate; incurving.

*Apex*.—Acuminate.

*Base*.—Cordate.

*Margin*.—Entire; not undulate to slightly undulate.

*Texture and luster, upper and lower surfaces*.—Smooth, glabrous; moderately glossy.

*Venation pattern*.—Pinnate, reticulate.

*Color*.—Developing leaves, upper surface: Close to 137B. Developing leaves, lower surface: Close to 138B. Fully expanded leaves, upper surface: Close to NN137A; venation, close to 137B. Fully expanded leaves, lower surface: Close to 137D; venation, close to 138C.

*Petioles*.—Length: About 1.2 cm. Diameter: About 1.8 mm. Texture, upper and lower surfaces: Smooth, glabrous. Color, upper and lower surfaces: Close to 144B.

Flower description:

*Flower type and habit*.—Single-type flowers; flowers face mostly outwardly; freely flowering habit with about seven flowers per axil and numerous flowers developing during the flowering season.

*Natural flowering season*.—Plants begin flowering about six weeks after planting rooted cuttings; long flowering period, plants flower continuously from summer until late autumn in Japan.

*Flower longevity on the plant*.—About seven to ten days; flowers not persistent.

*Fragrance*.—None detected.

*Flower buds*.—Height: About 6.4 cm. Diameter: About 1.4 cm. Shape: Rhombic. Color: Close to 62C.

*Flowers*.—Appearance: Single-type, five imbricate petals in a single whorl. Diameter: About 8.2 cm. Depth (length): About 7.5 cm. Throat diameter, distally: About 2.1 cm. Throat diameter, proximally: About 9.7 mm. Throat length: About 3.4 cm. Tube length: About 1.9 cm. Tube diameter, proximally: About 3.7 mm.

*Corolla*.—Quantity and arrangement: Five petals fused towards the base into an elongated throat and tube; petal lobes imbricate. Petal lobe length: About 3.3 cm. Petal lobe width: About 3.5 cm. Petal lobe shape: Spatulate, strongly asymmetrical. Petal lobe apex: Acute. Petal lobe margin: Entire; slightly undulate and slightly recurving. Petal lobe texture and luster, upper and lower surfaces: Smooth, glabrous; matte. Throat texture: Smooth, glabrous. Tube texture: Smooth, glabrous. Color: Petal lobe, when opening, upper surface: Close to 63C. Petal lobe, when opening, lower surface: Random sectors, close to 65A and 63B. Petal lobe, fully opened, upper surface: Random sectors, close to 63A and 63D; venation, similar to lamina colors; colors do not change with subsequent development. Petal lobe, fully opened, lower surface: Random sectors, close to 65C and 63C; venation, similar to lamina colors; colors do not change with subsequent development. Throat, inner surface: Distally, close to 63A, and proximally, close to 63A and 16B; venation, close to 63A. Throat, outer surface: Distally, close to 63D, and proximally, close to 63D and 144D; venation, similar to lamina colors. Tube, inner surface: Close to 14C; venation, close to 14C. Tube, outer surface: Close to 184B and 144D; venation, similar to lamina colors.

*Calyx*.—Quantity and arrangement: Five sepals arranged in a single whorl, fused at the base; calyx, star-shaped. Sepal length: About 4.9 mm. Sepal width: About 1.7 mm. Sepal shape: Lanceolate. Sepal apex: Acute. Sepal margin: Entire. Sepal texture, upper and lower surfaces: Smooth, glabrous. Sepal color, upper surface: Distally, close to 61D, and proximally, close to 144D. Sepal color, lower surface: Distally, close to 138C, and proximally, close to 138B.

*Peduncles*.—Length: About 2.5 cm. Diameter: About 1.9 mm. Texture: Smooth, glabrous. Aspect: Upright to outwardly. Color: Close to 138A.

*Pedicels*.—Length: About 1.7 cm. Diameter: About 2.4 mm. Texture: Smooth, glabrous. Aspect: Upright to outwardly. Color: Close to 138C.

*Reproductive organs*.—Stamens: Quantity: Five. Anther size: About 1.3 mm by 5.7 mm. Anther shape: Lanceolate. Anther color: Close to 8C. Amount of pollen: Scarce. Pollen color: Close to 8C. Pistils: Quantity: Typically one. Pistil length: About 2 cm. Style color: Close to 145C. Stigma shape: Conical. Stigma color: Close to 150C. Ovary color: Close to 145A.

*Seeds and fruits*.—To date, seed and fruit development have not been observed on plants of the new *Mandevilla*.

Pathogen & pest resistance: To date, plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 13872' as illustrated and described.

* * * * *